United States Patent [19]

Larson

[11] 4,419,166
[45] Dec. 6, 1983

[54] METHOD OF ASSEMBLING A FILTER HOLDER

[75] Inventor: Roger R. Larson, Champaign, Ill.

[73] Assignee: I-Temp Corporation, Decatur, Ill.

[21] Appl. No.: 80,945

[22] Filed: Oct. 1, 1979

Related U.S. Application Data

[62] Division of Ser. No. 925,630, Jul. 6, 1978, Pat. No. 4,191,654.

[51] Int. Cl.³ .............................................. B01D 25/04
[52] U.S. Cl. ................................ 156/272.4; 156/290; 210/445; 210/451
[58] Field of Search .............. 210/445, 505, 446, 490, 210/DIG. 23, 451; 264/25, 27; 156/272.4, 290

[56] References Cited

U.S. PATENT DOCUMENTS

| | | | |
|---|---|---|---|
| 3,156,645 | 11/1964 | Chapin et al. | 210/321 R X |
| 3,158,532 | 11/1964 | Pall et al. | 210/505 |
| 3,394,615 | 7/1968 | Brueder | 264/27 X |
| 3,457,171 | 7/1969 | Flowers et al. | 210/321 R X |
| 3,504,801 | 4/1970 | Alexander | 210/321 R |
| 3,567,031 | 3/1971 | Lueffler | 210/DIG. 23 |
| 3,615,024 | 10/1971 | Michaels | 210/490 |
| 3,954,625 | 5/1976 | Michalski | 210/445 |
| 3,963,845 | 6/1976 | Dukess | 264/25 X |
| 4,157,967 | 6/1979 | Meyst et al. | 210/DIG. 23 X |

Primary Examiner—Frank A. Spear, Jr.
Attorney, Agent, or Firm—Harvey B. Jacobson

[57] ABSTRACT

A device is disclosed for holding a membrane filter with use of a porous metal disk support for a membrane. In the method of assembly the metal disk and membrane are sealed to a fusible enclosure by heat formed in the metal disk by induction heating. Such heat seals the metal disk and also seals the surface of the membrane to the fusible surrounding enclosure. The device is particularly useful in filtering particulate matter from intravenous solutions administered into the circulatory system of a human.

3 Claims, 7 Drawing Figures

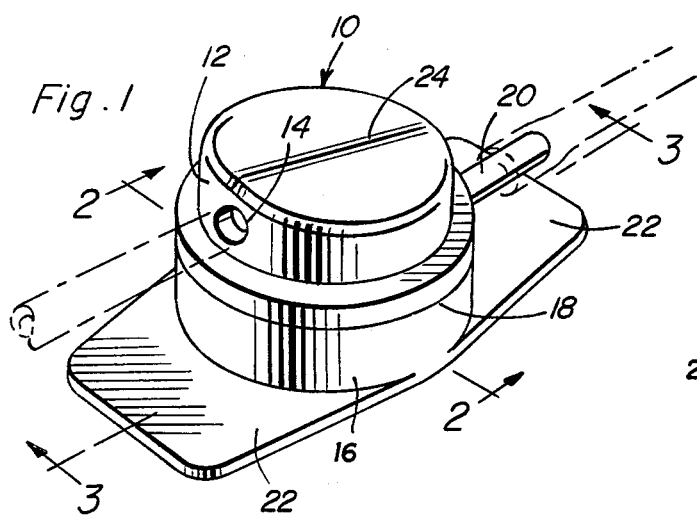
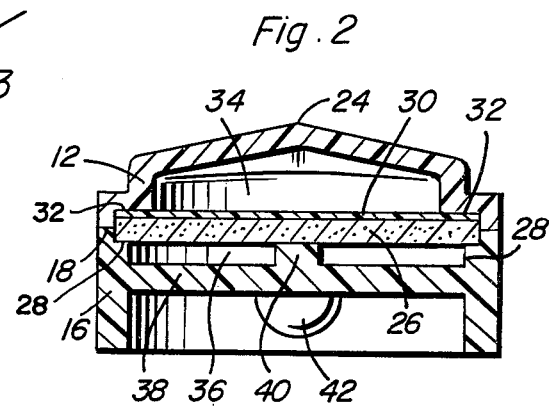
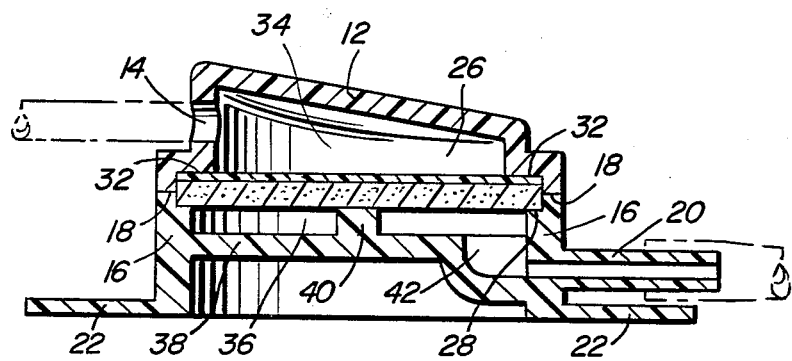
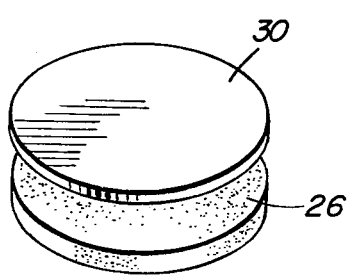
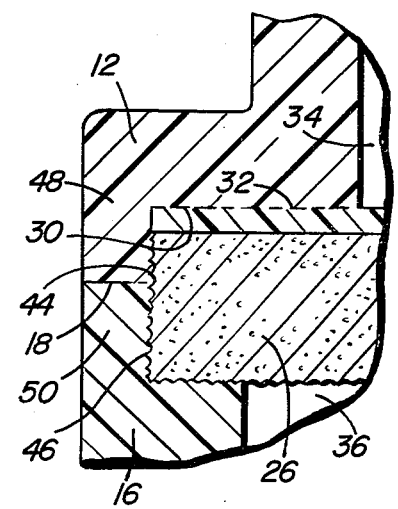
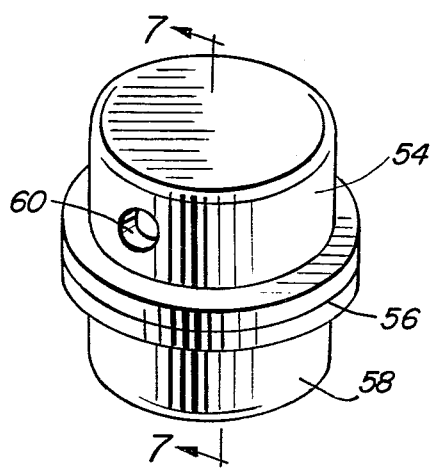
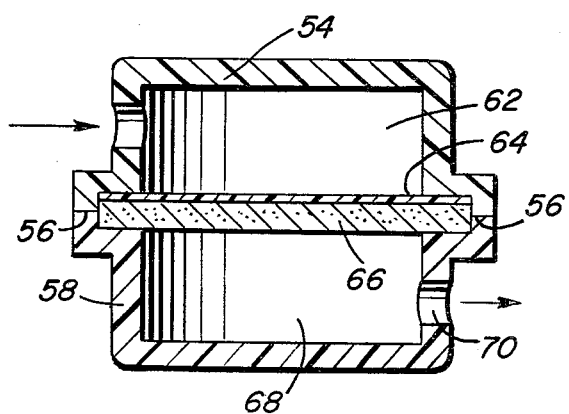

METHOD OF ASSEMBLING A FILTER HOLDER

This is a division, of application Ser. No. 925,630, filed July 6, 1978, now U.S. Pat. No. 4,191,654.

BACKGROUND OF THE INVENTION

1. Field of the Invention

The invenntion relates to a holder for membrane filters, such as is used to remove particulate matter from intravenous solutions entering the circulatory system of a human. The invention also relates to a method of assembling a membrane holder from a fusible enclosure by application of induction heating to heat a metal disk membrane support and seal the fusible enclosure to the disk and to the membrane.

2. Description of the Prior Art

Filters manufactured from high strength synthetic polymer materials can be formed by a process designed to achieve a structure consisting of an ultrathin skin containing micro screening pores supported by an extremely pervious substructure. Such filters having an ultrathin screening surface and highly porous support give extraordinarily high flow rates observed at very low pressures. The extremely small surface pore size insures the complete elimination of particulate matter, including bacteria and viruses, and the ultrafilters are particularly resistant to plugging and fouling by many industrial and medical fluids. Such filters have particular utility in removing particulate matter from intravenous solutions administered to a human, since such particulate matter can lead to serious deleterious medical effects. Holders developed for such filters, however, have had shortcomings and drawbacks.

Particularly for the medical applications outlined above, filter holders in an intravenous feed line have been developed, such as the device shown in U.S. Pat. No. 3,471,019, issued Oct. 7, 1969, to Trasen, et al., showing a filter unit sealed together by pressing two parts of a housing surrounding the filter, and fusing the sealing portions of the housing parts by ultrasonic welding. Many materials for construction of the filter holder have poor characteristics for ultrasonic sealing, or have poor characteristics for solvent welding. Furthermore, the filter unit of the Trasen et al patent requires a plurality of upstanding rib means to support the filter in order to enable it to withstand the pressure of fluid flowing therethrough without tearing.

Other patents showing filtering devices include U.S. Pat. Nos. 3,854,907 and 3,149,758.

SUMMARY OF THE INVENTION

In order to supply an ultrafilter membrane manufactured from synthetic polymer and having an extraordinarily high flow rate at very low pressures, a metal disk of the same size as the circular membrane filter is placed in contact with shelves of a fusible bottom holder, the membrane is placed in proper orientation on the metal disk, and a complementary upper fusible holder is then placed in position. Sealing is achieved by placing the assembled unit in a conventional heat induction device, which raises the metal disk, but not the non-metallic components, to a temperature sufficient to seal the enclosing material of the bottom and upper holder.

It is accordingly an object of the present invention to provide a membrane filter holder having a porous metal support disk in sealing engagement with a fusible enclosure.

Another object is to seal the filter holder by induction heating so as to prevent contamination of the filter, support disk, or enclosing means.

Still another object of the invention is to disclose a method for sealing the surface of the membrane to the enclosing material.

Yet another object of the invention is to provide a filter holder for use in filtering intravenous solutions administered into the circulatory system of a human.

A further object of the invention is to provide a filter unit which is sturdy, compact, light weight, easily manufactured by hand or automated assembly techniques, and hermetically sealed from air and outside contamination.

A still further object is to provide a method for making a membrane filter holder of the construction outlined herein.

These together with other objects and advantages which will become subsequently apparent beside in the details of construction and operation as more fully hereinafter described and claimed, reference being had to the accompanying drawings forming a part hereof, wherein like numerals refer to like parts throughout.

BRIEF DESCRIPTION OF THE DRAWING

FIG. 1 is a perspective view of a preferred embodiment of the present invention.

FIG. 2 is a transverse sectional view of the embodiment shown in FIG. 1, taken substantially upon a plane passing along section line 2—2 of FIG. 1.

FIG. 3 is a longitudinal sectional view of the embodiment shown in FIG. 1, taken substantially upon a plane passing along section line 3—3 of FIG. 1.

FIG. 4 is an enlarged, fragmentary sectional view of the filter holder of the present invention, showing details of the seal formed between components of the invention.

FIG. 5 is a group perspective view showing the relationship of a membrane filter with a porous metal support disk.

FIG. 6 is a perspective view of a second embodiment of the present invention.

FIG. 7 is a sectional view of the embodiment of FIG. 6, taken substantially upon a plane passing along section line 7—7 of FIG. 6.

DESCRIPTION OF THE PREFERRED EMBODIMENTS

A filter holder device, designated generally by the numeral 10, is shown in FIG. 1 in its assembled and completely sealed condition for use, and comprises upper enclosure 12 having inlet aperture 14, lower enclosure 16, sealed to upper enclosure 12 at interface 18 extending about the periphery of the device 10. Lower enclosure 16 contains an integral exit tube 20 for outward flow of filtered fluid, and also integral with lower enclosure 16 are support wings 22, which steady the device on a flat horizontal surface or when otherwise attached, such as to the body of a patient near a point of administration of intravenous fluid. Upper enclosure 12 has a peaked ridge 24 sloping downwardly in the backward direction in FIG. 1.

Porous metal disk 26, shown as a sintered stainless steel disk in FIGS. 2 and 3, is made with a thickness sufficient to put disk 26 in contact with shoulder 28 of lower enclosure 16, while placing the upper surface of a membrane 30 in contact with shelf 32 of upper enclosure 12. The region between the roof of upper enclosure 12 and the membrane 30 defines an upper filter chamber 34, where incoming fluid is collected for filtration through membrane 30 and porous metal disk 26. Filtered fluid collects in lower filter chamber 36, defined by metal disk 26 and lower enclosure base 38. Base 38 is provided with a central projection or knob 40 to assist in support of metal disk 26. At the end of base 38 opposite inlet aperture 14, depression 42, which is molded into lower enclosure 16, allows filtered fluid to be collected and transmitted into outlet tube 20 for use.

In sealing the component parts of the device, heat is transmitted from metal disk 26 to the inside surfaces 44 and 46 of lips 48 and 50 forming the enclosing means on upper enclosure 12 and lower enclosure 16, respectively as shown in FIG. 4. Metal disk 26 is heated by induction without substantial heating of non-metallic components of the device. As the temperature of metal disk 26 passes above the fusing temperature of the material constituting upper enclosure 12 and lower enclosure 16, fusing at the point of contact of disk 26 with the enclosures takes place. Such fusion is illustrated in FIG. 4 by the irregular outline at inside surface 44 of lip 48 and inside surface 46 of lip 50. In addition, the partial fusing at interface 18 is shown by the dotted line in FIG. 4 between upper lip 48 and lower lip 50 in the region nearest metal disk 26. Uniform fusing as described produces an airtight seal of the holder itself around interface 18, as well as around the edges of metal disk 26.

Membrane 30 can be chosen from a type described in the technical publication "Technical Information on Pharmapore Ultrafilters", published by Pharmaco, Inc., Champaign, Illinois. Such ultrafilters are manufactured from a high strength electrically neutral synthetic polymer, giving an isoporous filter with an asymmetric structure consisting of an ultrathin skin containing micro screening pores supported by an extremely pervious substructure, which is made up of vertical columns arranged in a honeycomb framework. This combination of ultrathin screening surface and highly porous support is responsible for extraordinarily high flow rates at very low pressures, making the filters particularly adaptable for the medical uses outlined above. It is possible to use such ultrafilters under ordinary gravity flow conditions without the need for high pressure generation systems. The extremely small surface pore size insures substantially complete elimination of particulate matter including bacteria and viruses. Moreover, the ultrafilters can be made to be resistant to plugging and fouling by many industrial and medical fluids encountered in practice. Filters of this type withstand temperatures generated in sealing of disk 26 to lips 48 and 50. During such application of heat by induction heating, the heat passes through membrane 30 to plastic shelf 32 of upper enclosure 12, causing the plastic on shelf 32 to melt and seal to the surface of membrane 30 in contact therewith. Such sealing action is illustrated in FIG. 4 by the dotted line between membrane 30 and shelf 32. Membrane 32, when selected from the ultrafilter type described above has a sieving action on its surface, unlike a depth filter, which requires a fluid to penetrate the entire membrane. Consequently, an ultrafilter is particularly adapted to use in the device 10 of the present invention, because sealing to shelf 32 is all that is necessary in order to achieve a proper seal. It is not necessary, therefore, that the peripheral edge of membrane 30 be sealed to plastic to prevent fluids from passing through the top of the filter and out the sides of the membrane filter. Such edge sealing is, of course, necessary when a conventional depth filter is to be sealed in a plastic holder device. In consequence of the requirements for the membrane 30 stated above, it is necessary that membrane 30 possess an ability to withstand higher temperatures than required to melt the material forming enclosures 12 and 16, and it is desirable that membrane 30 have the asymmetric structure leading to the advantageous filtration properties described.

Metal disk 26 can be made of one of many suitable non-toxic, non-fiber releasing metallic materials, such as a flat perforated metal disk, a sintered microporous metal disk, a sintered stainless steel disk, or other conventional porous metal disks known in the medical arts. Besides providing porous backup for membrane 30, metal disk 26 provides the mechanism for heat transmission to seal with the plastic enclosure. Sealing occurs in a single operation at a number of sites as heat is generated inductively in metal 26, namely, along shelf 32, around interface 18, and around inside surfaces 44 and 46.

With use of a porous metal plate or disk to provide necessary support structure, excellent machine control is also achieved for quick and easy heat application in a heat induction coil. A further advantage of the invention derives from the fact that the same operation which generates heat in the metal plate or disk for sealing the membrane surface to the plastic enclosure is also used to hermetically seal the parts of the holder about the interface contacting each portion of the enclosure. Furthermore, the device lends itself to either automated assembly or hand assembly.

In a second embodiment of the present invention, shown in FIGS. 6 and 7, upper enclosure 54 is sealed about interface 56 to lower enclosure 58, fluid entering upper enclosure 54 through aperture 60 into upper chamber 62, where the fluid contacts membrane 64 supported on porous metal disk 66. Filtered liquid is collected in lower chamber 68 and exits through exit aperture 70. Sealing between membrane 64 and upper enclosure 54, as well as sealing between disk 66 and peripheral ennclosures 54 and 58 is accomplished in the manner described above for the first embodiment of the invention. Sealing of the membrane 64 will accordingly closely resemble that illustrated in FIG. 4 in connection with the first embodiment of the invention.

When membrane 30 is selected from typical ultrafilters commercially available, one side of such ultrafilters can be seen to present a more reflective or shiny surface than the other surface. Preferably, the shiny surface of such membrane 30 should face downwardly against metal disk 26 in the first embodiment of the invention, or against metal disk 66 in the second embodiment in order to reduce or minimize rupture of membrane 30 during sealing.

When used in the administration of intravenous solution, it is important to avoid creation or existence of any air lock. The contour of the device shown in FIG. 1 is particularly adapted to avoiding such problems.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. A method of assembling a membrane filter holder having a filter assembly and enclosing means, the filter assembly comprising a membrane constructed of flat plastic sheet material, said membrane having a flat upper surface and a flat lower surface, substantially all of said lower surface contacting a flat porous metal support plate, and the enclosing means comprising an upper enclosure and a lower enclosure, said enclosures having opposed central recess portions and opposed sealing portions completely surrounding said central recessed portions, the upper closure having a shelf about the inside edge of said recessed portion and having an inlet aperture, said lower enclosure having an outlet aperture, said method comprising the steps of:

(a) aligning said upper enclosure and said lower enclosure on opposite sides of said filter assembly with an edge strip of the upper flat surface of said membrane contacting said shelf and said opposed sealing portions contacting each other and the periphery of said support plate;

(b) heating said metal support plate by induction heating, thereby heating said membrane to a temperature sufficient to melt said upper enclosure at said shelf; and (c) maintaining contact between said shelf and said edge strip until said edge strip is sealed continuously to said shelf, wherein said induction heating further raises the temperature of said metal support plate above the melting temperature of said opposed sealing portions, thereby causing said upper enclosure and said lower enclosure to form a fused seal at the contact point of said sealing portions adjacent said metal support plate.

2. The method of claim 1 wherein said enclosing means is formed of a thermoplastic.

3. The method of claim 1 wherein said membrane filter in an ultrafilter.

* * * * *